United States Patent [19]

Ries

[11] 4,055,171
[45] Oct. 25, 1977

[54] SPLINT
[75] Inventor: Douglas A. Ries, St. Louis, Mo.
[73] Assignee: Edward M. Ring, St. Louis, Mo.; a part interest
[21] Appl. No.: 706,743
[22] Filed: July 19, 1976
[51] Int. Cl.² .................................................. A61F 5/04
[52] U.S. Cl. ...................................... 128/87 R; 128/94
[58] Field of Search .................. 128/87 R, 88, 84 R, 128/85, 94, 77, 165

[56] References Cited

U.S. PATENT DOCUMENTS

| 161,323 | 3/1875 | Brown et al. ........................... 128/88 |
| 1,121,795 | 12/1914 | Burton ................................ 128/84 R |
| 1,340,630 | 5/1920 | Maddox ................................ 128/88 |
| 2,916,034 | 12/1959 | Detwiler ............................... 128/94 |
| 3,073,299 | 1/1963 | Detwiler ............................... 128/94 |
| 3,199,509 | 8/1965 | Smith .................................... 128/94 |

FOREIGN PATENT DOCUMENTS 5,763  4/1897  Norway .................................. 128/94

Primary Examiner—John D. Yasko
Attorney, Agent, or Firm—Rogers, Eilers & Howell

[57] ABSTRACT

A surgical splint for use in suspending the arm of a patient during axillary or chest area surgery, in different elevated positions, comprising a hooked support secured to the operating table for vertical adjustment, with slipping chain means suspending from the support a padded arm splint formed of channelled upper arm and forearm sections hinged together, to be strapped to the arm, and means to prevent the arm from slipping lengthwise from the splint.

14 Claims, 5 Drawing Figures

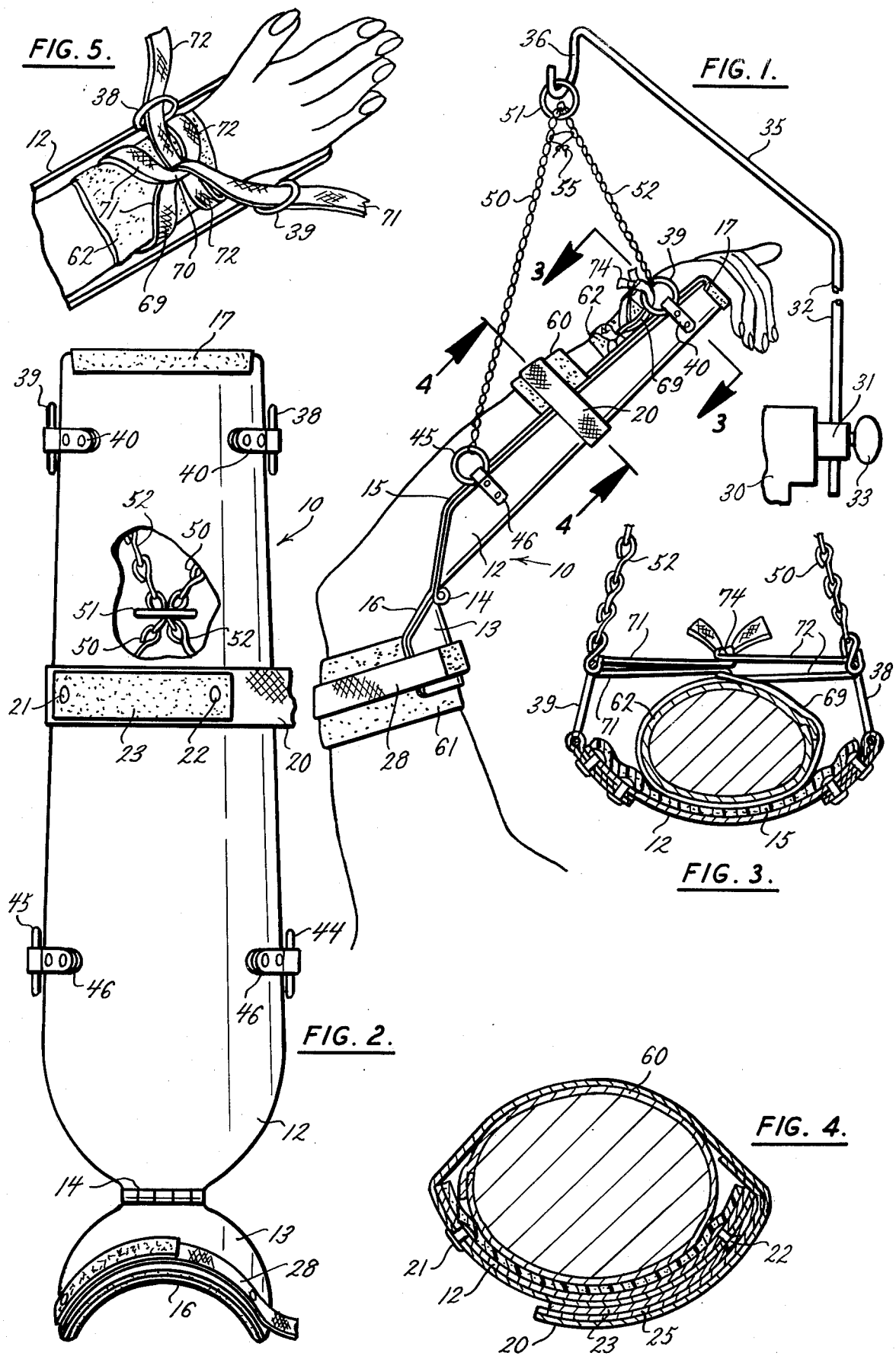

SPLINT

BACKGROUND OF THE INVENTION

In surgery in the axilla and chest areas, it is necessary to hold the arm of the patient elevated to an appropriate degree to give access to the excision areas. Heretofore, the practice has been to have the arm manually held elevated by a nurse or other assistant, a practice which is very tiring when the surgery takes an extended period of time.

The present device substitutes mechanical means for holding the arm in elevated position but provides also for an adjustment by which the arm can be held in any of several different positions appropriate to the surgery to be performed. It further holds the arm by means that are fixed relative to the operating table itself so that there is no relative movement between the holding means and the patient on the table. This avoids a problem with manual holding, of possible movement at an inopportune time on the part of the person holding the patient's arm. It also assures that the appropriate angle for the arm selected by the surgeon will be maintained constant throughout the surgery.

With the present device the arm may be positioned with the forearm fairly horizontal for superficial surgery, or more vertical for deeper work.

It will further be noted that the supporting means for the patient's arm as herein provided is out of the way of the surgeon during the surgery in the axillary or chest areas. This is the result of having the primary suspending means above the arm of the patient and connected to the operating table by a relatively narrow shepherd's crook type of support that is attached to the splint by suspending means.

Heretofore, splints have been made for example, for stabilizing broken bones but they would be largely impractical for the present purposes. For example, splints of the nature of U.S. Pat. No. 3,528,413 cannot well be used to hold an arm in a high position. Other devices such as in U.S. Pat. No. 3,256,880 are immobilizing splints that do not provide for any arm support for suspension. Some traction devices provide suspending means but do not provide for the holding in elevation by supporting the forearm and upper arm and particularly do not provide for the suspension of the arm in an adjustable manner that can modify the angle of the arm to the body, or the angle of the forearm to the upper arm.

In the drawings

FIG. 1 is an elevational view of the device in use, the operating table frame being shown diagrammatically;

FIG. 2 is a bottom view of the splint;

FIG. 3 is a transverse section on the line 3—3 of FIG. 1;

FIG. 4 is a transverse section on the line 4—4 of FIG. 1; and

FIG. 5 is a view illustrating the manner of making the wrist tie arrangement.

DESCRIPTION OF THE PREFERRED EMBODIMENT

The splint 10 consists of two principal components, a forearm section 12 and a smaller upper arm section 13, the two being hinged together at 14. Both of the two members 12 and 13 have curved channel cross sections so that they can receive the corresponding portions of the arm. The hinge 14 permits the two sections 12 and 13 to pivot in accordance with the relative positions of the forearm and upper arm of the patient. These two sections 12 and 13 are preferably made of a lightweight material such as aluminum, although other appropriate materials can be used.

Both the forearm section 12 and the upper arm section 13 are lined with a soft material such as a thick coating of a felt or other like padding, that is secured by adhesive to the concave surfaces of the members. The padding for the section 12 is illustrated at 15 and the padding for the section 13 is shown at 16. It is desirable to have the padding 15 on the forearm section 12 extend around the upper end as shown at 17, to aid in cushioning the hand, as will appear.

A Velcro strap 20 is riveted at 21 and 22 to the forearm section 12. It has the familiar Velcro attachment material 23 across its surface from side to side under the support. The free end of the strap 20 has Velcro mating material 25 that can be pressed against and secured to the material 23 to hold the end of the strap with any appropriate degree of tightness.

A similar Velcro strap 28 is attached to the upper arm section 13 and operates in a like manner to be drawn around the upper arm and secured with an appropriate degree of tightness.

The splint is adapted to be suspended by a support somewhat like a shepherd's crook that is adjustably attached to the operation table.

In the drawings the operating table, upon which the patient lies, is diagrammatically illustrated at 30 and is supported from the floor as is well known in the art. A sleeve bracket 31 extends securely from each of its side edges to receive a vertical shaft portion of the shepherd's crook support 32 which is made of appropriately strong metal. The vertical portion of the shepherd's crook 32 is inserted into the bracket 31 on the far side of the patient from the side to be operated upon, and is vertically adjusted within the sleeve 31 to an appropriate height, and secured in adjusted position by a wing nut 33 or other clamping means in a manner that is well understood in this art.

The upper end of the shepherd's crook is bent over laterally at 35 and has a hook 36 at its outer end. It is shaped so that it can extend sufficiently over the operating table 30 for purposes to be described, in which the splint is positioned to hold the arm of the patient upwardly over the operating table.

The connections by which the splint is supported from the shepherd's crook are as follows:

The forearm section 12 of the splint 10 has four rings attached to it. At its outer or distal end are rings 38 and 39. Each ring is held to the section 12 by clips 40 that are riveted to the member 12.

The proximal group of rings 44 and 45 are likewise held by clips 46 that are riveted to the member 12. The rings can freely swing in these clips.

Two chains are employed. A first chain 50 is attached at its ends to the rings 38 and 45, between which it passes through another ring 51. The other chain 52 is attached at its ends to the rings 39 and 44, and also passes through the ring 51. Thus, the chains cross over at the ring 51. With this arrangement, the ring 51 can be dropped over the hook 36 to hold the splint suspended from the shepherd's crook. A cord or like restraining means 55 may be tied around the chains adjacent the ring 51, to prevent slippage.

Three Kryex, or other pads such as foam rubber, are used. One such pad 60 as shown in FIG. 4, is wrapped around the forearm under the Velcro strap 20 to keep the Velcro strap from binding on the arm. A like pad 61 is wrapped around the distal upper arm to keep the strap 28 from binding. The third pad 62 may be wrapped around the hand adjacent the ring 38 and 39 to give some degree of protection from the tape, to be described. A preferable form of this is to use a Kryex roll which is somewhat resilient and non-occlusive.

Means to hold the arm against longitudinal slipping consists of a wide tape, such as a cloth tape, or other like strap 69, that holds the wrist.

As shown in FIG. 5, the single tape 69 is grasped and drawn by the middle across the forearm, making a loop 70 as shown in FIG. 5. The ends 71 and 72 of the tape are both then carried around the wrist and are passed through the loop 70. The end 71 is drawn out over the wrist to one side and passed through the ring 39, and the end 72 is passed through the ring 38. These two ends are then brought together and tied above the wrist in a knot 74 (FIG. 3) that can be easily loosened.

The use of the device is as follows:

The patient is caused to lie upon the operating table 30 to which the vertical rod 32 of the shepherd's crook is attached. The crook is mounted on the side of the table away from the operator, i.e., on the side opposite the axilla to be operated upon. (In FIG. 1, the drawing of the table 30 is greatly foreshortened).

The tape 69 is looped around the wrist and the ends extended out above the wrist, with its ends free. The Kryex pads 60, 61 and 62 are wrapped around the patient's arm and the splint placed appropriately against the arm. The Velcro straps 20 and 28 are secured around the forearm and upper arm with the appropriate degree of tension to hold the splint and arm together. The ends 71 and 72 of the tape 69 are passed through their respective rings 39 and 38 and tied above the wrist with a readily releasable knot (FIG. 3). The tape 69 is drawn tight enough to hold the wrist and keep it extended so that the arm does not slip lengthwise in the splint.

The ring 51 through which the two chains 50 and 52 pass is placed over the hook 36 of the shepherd's crook support 32. By raising or lowering the support 32 in the bracket 31, the patient's arm is drawn upwardly as far as necessary for the surgery in question. In the event of more superficial surgery at or near the skin, the support 32 is lowered to dispose the forearm more into a horizontal position.

If the work is to be done in the deeper structures, the shepherd's crook support 32 is raised, which automatically causes the arm and the splint to be tilted to a more vertical position, which is accommodated by the slipping of the chains through the ring, lowering the side rings 44 and 45 relative to the distal side rings 38 and 39. When the arm is appropriately raised and is in the desired position, the ring nut 33 is tightened. This elevation of the arm may be so extended as to stretch the soft tissues of the shoulder region and to draw the fat and connective tissues around the vessels and nerves adjacent the ribs that may be the object of an excision. This also will give ready access to the axilla, the upper arm and the deeper structures of the axilla.

By virtue of having the shepherd's crook and, therefore, the splint firmly secured to the operating table supporting frame, the arm is held in constant position throughout the necessary time of the operation and despite any movements accidental or otherwise to the operating table. Normally the nature of the chains is such that they stay in position in the ring 51, and this is a reason for preferring chains to any other form of support. It is desirable at times to tie a cord around the chains adjacent the hook 51, to insure against any slippage.

When the instrument is thus used, the surgeon has full access to the patient, as the only part that extends anywhere near the work area of the surgeon is the vertical rod of the support 32, which may be relatively small, and should be on the opposite side of the patient. There is no problem of movement by a person holding the arm, voluntarily or involuntarily, as occurred in former practices. The adjustments of the device are simple, involving mainly the elevation of the support 32 and the adjustment of the chains 50 and 52 in the central ring 51. The straps are all adjustable to accommodate arms of different sizes.

This splint has been described as having two chains that are crisscrossed to form a suspending means by which the splint is secured to the shepherd's crook support. In this action, as the support is raised, the chain remains in the ring 51. While other suspending means than chains can be used, as noted, chains have the advantage of being very flexible and also the advantage that they tend to remain in an adjusted position because of the relationship of the links to the ring 51. This minimizes the chance of slippage or the changing of the position of the patient's arm during the surgery.

The crossing over of the two chains from one side of the splint to the other is preferred, as it holds the splint and the arm against being twisted during surgery. The twisting of the forearm as it is raised enables the surgeon to get the proper positioning for surgery. This twisting action is accommodated by the lengthening of the ends of the chain on one side of the splint compared to their length on the other side.

Some of the advantages, but not all, of the present suspending arrangement could be obtained otherwise, as will be apparent. Primarily the suspending means comprises any flexible connection in the form of chain-like devices, cords or cables, having ends connected to the distal and proximal ends of the splint. It is desirable that the basic connector be of one piece, so that its mid-portion can be suspended over a hook. Preferably further, there are two such connectors that have their opposite ends connected to the opposite ends of the splint, and in further preference, crisscrossed as illustrated. If the connectors provide separate ends, the adjustment can be obtained provided they can be secured to the hook at different points on each, as by looping the links over the hook. This, however, is less desirable because it does not automatically adjust to the angular conditions of the arm as the support crook is raised and lowered.

Thus there are four chain ends connected to the opposite sides of the splint, all four being brought up to the ring 51, and in the preferred form the free ends are actually two connectors that are crossed over through a ring. The ring thus constitutes a connecting means between the chain ends. This arrangement is preferred to the one wherein, for example, a shorter chain were connected across between the two distal rings and another short chain between the two proximal rings and a longer chain then connected from each of the two short chains up through the ring 51.

The use of the upper arm member 13 stabilizes the splint. When the arm is bent, as it is in practically all usages of this device, the upper arm member and its strap aid in preventing the splint from slipping off the arm longitudinally.

Various changes and modifications may be made within this invention as will be readily apparent to those skilled in the art. Such changes and modifications are within the scope and teaching of this invention as defined by the claims appended hereto.

What is claimed is:

1. In a surgical splint to suspend a patient's arm during operations, the combination of: an elongated splint member of relatively stiff material resistant to longitudinal collapse, having a forearm portion of length to extend along the forearm from adjacent the wrist of the patient to adjacent the elbow; means to secure the patient's arm to the forearm portion of the splint member against slippage longitudinally of the member when the member with the arm is raised; at least one elongated flexible connector attached at one end to the splint adjacent the wrist end and attached at its other end to the splint member adjacent the elbow end thereof; a suspending support extending above the splint and vertically adjustable, the support having a hanger element onto which the connector is hung, and across which the connector may be moved to change the ratio of the distance along the connector from the hanger to the elbow relative to the distance from the hanger to the wrist, as the suspending support is raised and lowered without raising the body of the patient.

2. A splint of claim 1, with an upper arm extension hinged to the elbow and of the forearm portion, to extend along the upper arm at angles to the forearm portion, and means to secure the upper arm portion to the upper arm of the patient.

3. In the splint of claim 1: the splint member having rings at its proximal and distal ends, the connector being attached at its ends to the rings; and the means to secure the patient's arm to the splint being likewise mounted in said rings.

4. In the splint of claim 3: the last-named means to secure comprising a tie engageable over the wrist of the patient whose fingers extend around the distal end of the splint.

5. In the splint of claim 1: two connectors being used, each extending from adjacent the proximal to adjacent the distal end of the splint, and both being suspended by the suspending support.

6. In the splint of claim 1: the splint member being of curved cross section, and having its concave surface padded, the means to secure the patient's arm comprising strap means secured to the split member for engagement around the arm of the patient.

7. In the splint of claim 5: the connectors being flexible chains.

8. In the splint of claim 7: the splint member being made of thin metal, and having four rings, two on opposite sides at its distal end, and two at opposite sides of its proximal end, the ends of the chains being connected with the four rings.

9. In the splint of claim 5: with means to hold the connector members in selected positions with respect to the ring.

10. In the splint of claim 5: rings at each end of the splint on opposite sides thereof, into which the connectors are fastened.

11. In the splint of claim 10: each connector extending from the proximal end of the splint on one side thereof to the distal end on the other side.

12. In the splint of claim 2: the means to secure the splint to the arm comprising straps with quick-acting releasable connecting means at the end thereof.

13. In the splint of claim 1: the suspending support comprising a rod-like substantially vertical member attachable to an operating table for vertical adjustment, a portion at the top thereof extending at an angle to overlie a patient on the table; and havng a hook means to hold the hanger element.

14. In the splint of claim 13, the hanger element comprising a ring engageable over the hook means.

* * * * *